May 29, 1962 E. S. BOERNER Plant Pat. 2,149
ROSE PLANT
Filed May 26, 1961
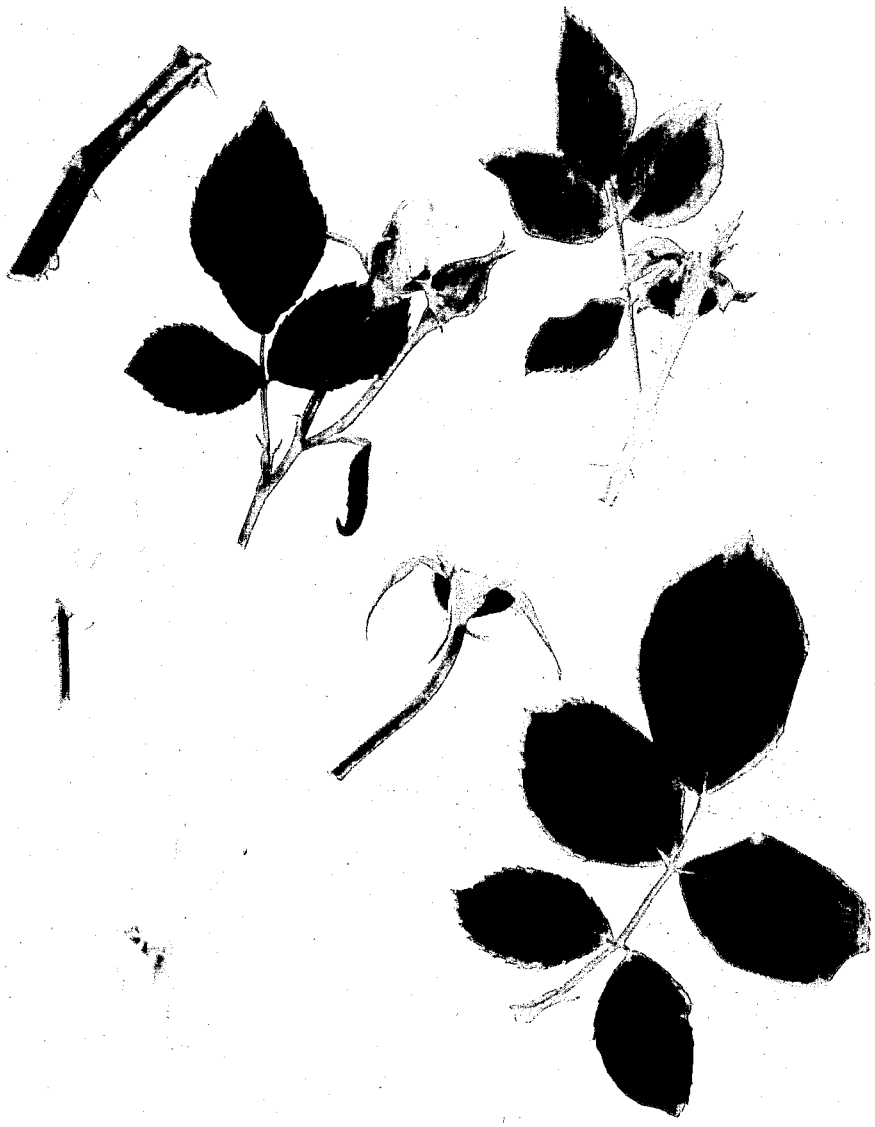
Inventor.
E. S. Boerner
By: Robb & Robb
Attorneys.

United States Patent Office

Plant Pat. 2,149
Patented May 29, 1962

2,149
ROSE PLANT

Eugene S. Boerner, Newark, N.Y., assignor to Jackson & Perkins Company, Newark, N.Y., a corporation of New York Filed May 26, 1961, Ser. No. 113,048
1 Claim. (Cl. 47—61)

The present invention relates to a new and distinct variety of rose plant of the Floribunda class, which was originated by me by crossing the variety "Spartan" (Plant Patent No. 1,357) with the variety "Pink Garnette" (Plant Patent No. 913).

The primary objective of this breeding was to produce a new rose variety of the floribunda type, but which has the prolific blooming habits of the parent variety "Spartan" in a different shape and form. This objective was fully achieved, along with other desirable improvements, as evidenced by the following unique combination of characteristics which are outstanding in the new variety and which distinguish it from its parents, as well as from all other varieties of which I am aware:

(1) A vigorous and upright habit of plant growth;

(2) A very free blooming habit, with consequent production of blooms throughout the summer;

(3) Flower petals which are stiffer than those of the parent variety "Spartan"; and (4) A distinctive and attractive two-toned pink general color tonality of the flowers corresponding to Thulite Pink, lightly overcast with Spinel Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Spartan."
*Pollen parent.*—"Pink Garnette."
Classification:
*Botanic.*—Floribunda.
*Commercial.*—Floribunda.

*Flower*

(Observations made from specimens grown outdoors at Newark, New York, in the early afternoon during the latter part of the month of August.)

Blooming habit: Recurrent—continuous.
Bud:
*Size.*—Medium.
*Form.*—Ovoid; is not affected by wet or hot weather.
*Color.*—When sepals first divide—Spinel Pink, Plate 26, lightly overcast with Spinel Red, Plate 26. When petals begin to unfurl—Spinkel Pink, Plate 26, lightly overcast with Thulite Pink, Plate 26. When half-blown: inside of petals—Thulite Pink, Plate 26, very lightly overcast with Spinel Pink, Plate 26; reverse of petals—Rose Red, Plate 12, lightly overcast with Spinel Pink, Plate 26.
*Sepals.*—Slightly branched; curl back when petals begin to unfurl. Color: inside—Kildare Green, Plate 31, with lower half of sepal lightly overcast with Glass Green, Plate 31; outside—Bice Green, Plate 17, with edge of sepal Acajou Red, Plate 13.

*Calyx.* — Color — Light Bice Green, Plate 17. Shape—funnel. Aspect — smooth. Size — long. Odor when rubbed—none.
*Peduncle.*—Length — medium. Aspect — smooth. Strength—erect; slender. Color—Corinthian Red, Plate 27.
*Opening.*—Opens up well; is not affected by adverse weather conditions.
Bloom:
*Size.*—Medium. Average size when fully expanded—from 3 inches to 3½ inches.
*Borne.*—Both singly and several together; very free blooming.
*Stems.*—Medium length; normal strength.
*Form (when first open).*—Open. Permanence—retains its form to the end.
*Petalage.*—Double (full but open center).—Number of petals under normal conditions—from 30 to 35.
*Color.*—Center of flower—Thulite Pink, Plate 26, with lower half of petal lightly overcast with Spinel Pink, Plate 26. Outer petals—Hermosa Pink, Plate 1, lightly overcast with Cameo Pink, Plate 1. Base of petals (aiglet)—Sea-Foam Yellow, Plate 31. Inside of petals—Thulite Pink, Plate 26. Reverse of petals—Rose Pink, Plate 12, lightly overcast with Cameo Pink, Plate 26. General tonality from a distance—Thulite Pink, Plate 26, very lightly overcast with Spinel Pink, Plate 26.
*Discoloration.*—General tonality at end of first day—Thulite Pink, Plate 26, very lightly overcast with Spinel Pink, Plate 26. Second day—Thulite Pink, Plate 26. Third day—Thulite Pink, Plate 26.
Petals:
*Texture.*—Leathery; stiff; is not affected by wet or hot weather.
*Appearance.*—Inside—satiny. Outside—shiny.
*Form.*—Oval; notched.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.* — On the plant — long. As cut flower—long.

*Genital Organs*

Stamens, anthers: Small; many; regularly arranged around styles. Color—Orange Buff, Plate 3.
Stamens, filaments (threads): Medium length. Color—Pale Salmon Color, Plate 14.
Pollen: Color—Pale Yellow-Orange, Plate 3.
Styles: Loosely separated; uneven length; medium length; thin.
Stigmas: Color—Maize Yellow, Plate 4.
Ovaries: All enclosed in calyx.
Hips: None.
Seeds: None.

*Plant*

Form: Bush.
Growth: Vigorous; upright.
Foliage: Compound of 3–5 leaflets.
*Size.*—Medium.
*Quantity.*—Normal.
*Color.*—New foliage: upper side—Parrot Green, Plate 6, lightly overcast with Acajou Red, Plate 13; under side—Yellowish Oil Green, Plate 5, overcast with Eugenia Red, Plate 13, on the outer edge. Old foliage: upper side—Bice Green, Plate 17; under side—Light Bice Green, Plate 17.
*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Acajou Red, Plate 13. Under side—prickly.

*Stipules.*—Medium length; bearded.

Wood:

*New wood.*—Color—Light Lumiere Green, Plate 17. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; short; hooked downward. Color (when young)—Alizarine Pink, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a vigorous and upright habit of plant growth, a very free blooming habit, with consequent constant production of blooms throughout the summer, stiffer flower petals than those of the parent variety "Spartan" (Plant Patent No. 1,357), and a distinctive and attractive two-toned pink general color tonality of the flowers corresponding to Thulite Pink, lightly overcast with Spinel Pink.

No references cited.